United States Patent
Avellanet et al.

[11] Patent Number: 6,019,736
[45] Date of Patent: Feb. 1, 2000

[54] GUIDEWIRE FOR CATHETER

[75] Inventors: Francisco J. Avellanet, 11024 SW. 77 Court Cir., Miami, Fla. 33156; Robert Braun, Palm Beach Gardens, Fla.

[73] Assignee: Francisco J. Avellanet, Miami, Fla.

[21] Appl. No.: 08/856,571

[22] Filed: May 15, 1997

Related U.S. Application Data

[63] Continuation-in-part of application No. 08/554,336, Nov. 6, 1995, abandoned, which is a continuation-in-part of application No. 08/730,489, Oct. 11, 1996, abandoned.

[51] Int. Cl.[7] .................................................. A61B 5/00
[52] U.S. Cl. .......................... 600/585; 604/96; 604/280
[58] Field of Search ............................... 600/585; 604/95, 604/96, 280, 281, 282; 433/20

[56] References Cited

U.S. PATENT DOCUMENTS

| | | | |
|---|---|---|---|
| H1239 | 10/1993 | Dusek | 264/63 |
| 251,114 | 12/1881 | Hallidie . | |
| 1,742,172 | 12/1929 | Atwood . | |
| 1,888,076 | 11/1932 | Evans . | |
| 1,888,807 | 11/1932 | Rivers . | |
| 1,904,162 | 4/1933 | Milliken . | |
| 1,943,082 | 1/1934 | MacKenzie | 261/49 |
| 1,943,086 | 1/1934 | McKnight | 173/264 |
| 1,943,087 | 1/1934 | Potter | 173/264 |
| 2,071,709 | 2/1937 | Riddle | 117/16 |
| 2,135,800 | 11/1938 | Davignon | 88/52 |
| 2,154,551 | 4/1939 | Wodtke | 174/128 |
| 2,156,652 | 5/1939 | Harris | 57/145 |
| 2,396,734 | 3/1946 | Williams | 174/128 |
| 2,427,507 | 3/1947 | Powell, III et al. | 57/161 |
| 2,978,860 | 4/1961 | Campbell | 57/148 |
| 3,083,817 | 4/1963 | Campbell | 205/2 |
| 3,130,536 | 4/1964 | Peterson et al. | 57/161 |
| 3,131,469 | 5/1964 | Glaze | 29/470.5 |
| 3,195,299 | 7/1965 | Dietz | 57/149 |
| 3,234,722 | 2/1966 | Gilmore | 57/145 |
| 3,295,310 | 1/1967 | Beighley | 57/145 |
| 3,352,098 | 11/1967 | Gilmore | 57/147 |
| 3,383,704 | 5/1968 | Schoerner et al. | 57/145 |
| 3,395,528 | 8/1968 | Lucht et al. | 57/145 |
| 3,444,684 | 5/1969 | Schoerner et al. | 57/161 |
| 3,601,970 | 8/1971 | Roberts et al. | 57/153 |
| 3,699,768 | 10/1972 | Roberts et al. | 57/144 |
| 3,812,666 | 5/1974 | Sarracino | 57/58.52 |

(List continued on next page.)

FOREIGN PATENT DOCUMENTS

| | | | |
|---|---|---|---|
| 0 480 427 A1 | of 1991 | European Pat. Off. | A61M 25/01 |
| 0 649 636 A2 | of 1994 | European Pat. Off. | A61B 17/82 |
| 0 649 636 A3 | of 1994 | European Pat. Off. | A61B 17/82 |
| 0 666 086 A1 | of 1994 | European Pat. Off. | A61M 25/00 |
| 0642 876 A1 | 8/1994 | European Pat. Off. . | |
| 0 537 618A1 | 4/1996 | European Pat. Off. . | |
| 595245 | 4/1934 | Germany . | |
| 197692 | of 1923 | United Kingdom | 174/128.1 |
| 278233 | 10/1927 | United Kingdom . | |

OTHER PUBLICATIONS

Suhner, How to produce efficiently flexible shafts and casings; May/Jun. 1978, WIRE, pp 109–112.

Fogiel, Modern Microelectronics, 1972, pp 735–737.

Kelly, A Plating Process for Ensuring Component Lead Solderability, SMT, Oct. 1997, pp 68,70.

*Primary Examiner*—Cary O'Connor
*Assistant Examiner*—Pamela Wingood
*Attorney, Agent, or Firm*—David P. Gordon; David S. Jacobson; Thomas A. Gallagher

[57] ABSTRACT

A flexible intravascular guidewire comprises a plurality of filaments braided together and drawn through a die to a reduced cross-sectional area of circular shape. Preferably, one or more of the filaments is coated with a radiopaque material prior to drawing it through the dye. According to a preferred embodiment, each of the filaments is made from the same metallic material; alternatively, the filament material may differ, e.g., to provide flexibility and torsional stiffness characteristics which are unachievable in a metal monofilament, or in a multifilament wire of the same filament materials.

28 Claims, 3 Drawing Sheets

U.S. PATENT DOCUMENTS

| | | | |
|---|---|---|---|
| 3,813,370 | 5/1974 | Gilmore | 57/145 |
| 3,822,542 | 7/1974 | Naud et al. | 57/145 |
| 3,842,185 | 10/1974 | Raw et al. | 174/23 R |
| 3,883,278 | 5/1975 | Hass | 425/135 |
| 3,883,371 | 5/1975 | Geary | 148/32 |
| 3,900,347 | 8/1975 | Lorenzetti et al. | 148/12 B |
| 3,922,841 | 12/1975 | Katsumata et al. | 57/145 |
| 3,923,003 | 12/1975 | Carden | 118/405 |
| 3,934,446 | 1/1976 | Avitzur | 72/206 |
| 3,942,309 | 3/1976 | Cahill | 57/9 |
| 3,955,390 | 5/1976 | Geary | 72/64 |
| 3,961,514 | 6/1976 | Geary | 72/274 |
| 3,972,304 | 8/1976 | Boucher | 118/44 |
| 3,990,874 | 11/1976 | Schulman | 65/4 B |
| 4,020,829 | 5/1977 | Willson et al. | 128/2 M |
| 4,079,510 | 3/1978 | McGrath et al. | 29/624 |
| 4,125,741 | 11/1978 | Wahl et al. | 174/120 |
| 4,133,167 | 1/1979 | Schofield | 57/12 |
| 4,173,235 | 11/1979 | Tipper | 140/82 |
| 4,201,250 | 5/1980 | Walling et al. | 141/250 |
| 4,212,151 | 7/1980 | Schauffelle et al. | 57/9 |
| 4,215,703 | 8/1980 | Willson | 128/772 |
| 4,311,001 | 1/1982 | Glushko et al. | 51/215 |
| 4,328,662 | 5/1982 | Bretegnier et al. | 57/58.61 |
| 4,330,956 | 5/1982 | McCarthy | 43/4 |
| 4,349,694 | 9/1982 | Vives | 174/128 R |
| 4,352,697 | 10/1982 | Adams et al. | 148/2 |
| 4,354,880 | 10/1982 | Adams et al. | 148/2 |
| 4,406,058 | 9/1983 | Dixon | 29/809 |
| 4,456,491 | 6/1984 | Adams et al. | 148/2 |
| 4,471,527 | 9/1984 | Nishijima | 29/872 |
| 4,473,995 | 10/1984 | Gentry | 57/9 |
| 4,514,058 | 4/1985 | Walton | 350/96.23 |
| 4,525,598 | 6/1985 | Tsukamoto et al. | 174/128 R |
| 4,529,837 | 7/1985 | Borden | 174/128 |
| 4,534,363 | 8/1985 | Gold | 128/772 |
| 4,548,206 | 10/1985 | Osborne | 128/772 |
| 4,579,127 | 4/1986 | Haacke | 600/585 |
| 4,634,042 | 1/1987 | Smith | 228/173.4 |
| 4,651,513 | 3/1987 | Dambre | 57/217 |
| 4,654,477 | 3/1987 | Isoda | 174/128 R |
| 4,679,387 | 7/1987 | Weidenhaupt et al. | 57/212 |
| 4,682,607 | 7/1987 | Vaillancourt | 128/772 |
| 4,689,444 | 8/1987 | Burgess | 174/128 R |
| 4,705,096 | 11/1987 | Chia | 164/476 |
| 4,731,134 | 3/1988 | Alloin et al. | 156/53 |
| 4,759,806 | 7/1988 | Dambre | 148/12 B |
| 4,778,246 | 10/1988 | Carroll | 350/96.23 |
| 4,843,696 | 7/1989 | Gentry et al. | 29/33 F |
| 4,922,924 | 5/1990 | Gambale | 128/772 |
| 4,925,445 | 5/1990 | Sakamoto | 604/95 |
| 5,018,993 | 5/1991 | Durham | 439/801 |
| 5,032,080 | 7/1991 | Hakansson et al. | 433/8 |
| 5,069,217 | 12/1991 | Fleischhacker | 128/657 |
| 5,074,140 | 12/1991 | Sanders | 72/248 |
| 5,129,890 | 7/1992 | Bates | 604/281 |
| 5,133,121 | 7/1992 | Birbeck et al. | 29/872 |
| 5,147,662 | 9/1992 | Nishijima et al. | 425/500 |
| 5,174,302 | 12/1992 | Palmer | 600/585 |
| 5,343,934 | 9/1994 | Wilson | 164/476 |
| 5,344,315 | 9/1994 | Hanson | 433/20 |
| 5,368,661 | 11/1994 | Nakamura et al. | 148/512 |
| 5,417,690 | 5/1995 | Sennett | 606/61 |
| 5,418,333 | 5/1995 | Sanders | 174/129 |
| 5,429,139 | 7/1995 | Sauter | 128/772 |
| 5,433,200 | 7/1995 | Fleischhacker | 128/657 |
| 5,437,288 | 8/1995 | Schwartz | 128/772 |
| 5,437,748 | 8/1995 | Bhagwat et al. | 148/532 |
| 5,439,000 | 8/1995 | Gunderson | 128/664 |
| 5,451,718 | 9/1995 | Dixon | 174/102 R |
| 5,486,183 | 1/1996 | Middleman et al. | 606/127 |
| 5,520,194 | 5/1996 | Miyata et al. | 128/772 |
| 5,535,612 | 7/1996 | Vijayakar | 72/43 |
| 5,571,086 | 11/1996 | Kaplan | 604/96 |
| 5,571,087 | 11/1996 | Ressemann | 604/96 |
| 5,571,094 | 11/1996 | Sirhan | 604/284 |
| 5,588,443 | 12/1996 | Davidson | 128/772 |
| 5,597,378 | 1/1997 | Jervis | 606/78 |
| 5,616,197 | 4/1997 | Helfer et al. | 152/527 |
| 5,709,760 | 1/1998 | Prakash | 152/556 |

GUIDEWIRE FOR CATHETER

This application is a continuation in part of Ser. No. 08/554,336 filed Nov. 6, 1995, now abandoned, which is a continuation in part of Ser. No. 08/730,489 filed Oct. 11, 1996.

BACKGROUND OF THE INVENTION

FIELD OF THE INVENTION

This invention relates to medical devices. More specifically, it relates to improvements in interventional guidewires of the type adapted to be advanced through arterial and other relatively narrow passageways of the human and animal body for the purpose of facilitating the insertion and placement of various medical devices and instruments, such as catheters, stents, drains, cystoscopes, dilators, etc., into various organs and body cavities to perform delivery or withdrawal of fluids, removal of tissue samples for biopsy or surgery, etc.

DESCRIPTION OF RELATED PRIOR ART

The use of a steerable guidewire to facilitate catheterization of various organs is commonplace in medical practice and, over the years, the guidewire design has taken a variety of forms. In general, however, such guidewires are usually composed of two sections, viz., a relatively stiff, yet still very flexible, proximal or "core" portion which is adapted to be pushed, pulled, twisted and otherwise manipulated by the medical practitioner for the purpose of advancing the wire through the intricate and tortuous passageways of the cardiovascular system, and a significantly more supple "distal" portion which is connected to the forward end of the core portion and functions to seek and follow different vascular pathways as the core portion is advanced behind it. Typically, the core portion of the guidewire is composed of a single strand (i.e., a monofilament) of metal, usually made of stainless steel or nickel-titanium alloy, having a length of between 125 and 300 cm., and a diameter of between about 0.25 and 1.0 mm. Like the core portion, the distal portion is usually comprised of a monofilament of the same metals, but, in contrast with the core portion, the distal portion is usually only about 1.0 and 3.0 cm. in length, and its diameter tapers from a diameter substantially equal to that of the core portion down to as low as 0.07 mm. Usually, the very tip of the distal portion is connected to a relatively bulbous member of much greater diameter, thereby providing the guidewire with a blunt and rounded end which serves to prevent the guidewire end from perforating or otherwise traumatizing the vascular wall as the guidewire is advanced by the user.

The "steerability" of a guidewire, i.e., its ability to react to torquing and pushing forces applied by the user so that the distal end may be manipulated into passageways of interest, is primarily determined by the wire's torsional stiffness and its column strength. Ideally, when the user torques or rotates the wire's core portion about its longitudinal axis at a location substantially displaced from the wire's distal tip, the distal tip should rotate through the same torque angle so that the user can sense or gauge what is happening to the distal tip as he or she rotates the wire's core portion. In principle, there should be a one-to-one correspondence between the torque angle applied by the user and the angular rotation of the distal end. Thus, to approach this ideal, it is recognized that a guidewire should exhibit an exceptionally high torsional stiffness, the higher, the better. On the other hand, the wire's column strength must be such as to provide the wire with sufficient stiffness to enable it to be pushed through lesions or other obstructions in the vascular passageways, yet provide the wire with sufficient flexibility as to enable the wire to follow an arterial passageway without causing trauma or, worse yet, a perforation. Thus, it will be appreciated that the ideal column strength of a guidewire is a trade-off between these competing traits. The simplest approach for increasing a guidewire's flexibility is to reduce its diameter. But, there is a limit to this approach in that, below a certain diameter, the guidewire cannot be viewed on a fluoroscope, the instrument conventionally used to visualize the movement of the wire. Moreover, below a certain diameter, the wire becomes so flexible as to have virtually no pushability, in which case the wire readily folds back on itself and kinks.

As noted above, virtually all guidewires have been made of a monofilament of either of two metal alloys, namely, either 304V stainless steel (available from Standard Press Steel, Jenkintown, Pa.) or a nickel-titanium alloy (available from Nitinol Devices & Components, Fremont, Calif.) While each of these materials affords certain advantages, neither can be considered optimal. For example, stainless steel alloys, while readily available and relatively inexpensive, exhibit relatively little torsional stiffness; as a result, guidewires made of this material tend to transmit only a fraction of the angular torque applied at one end to the other. Thus, the user can have difficulty in controlling the rotational position of the distal end of a stainless steel guidewire by torquing the core portion. Further, stainless steel has little shape memory and, as a result of being bent or otherwise distorted in shape, stainless steel guidewires tend to retain the distorted shape rather than returning to their original shape. Finally, stainless steel guidewires exhibit a relatively high column strength and, as a result, have little flexibility unless ground to a very small diameter, at which the wire's mass becomes so low as to render it difficult to view fluoroscopically. While a monofilament of nickel-titanium is advantageous in that it has greater torsional stiffness than stainless steel and exhibits a highly desirable resistance to permanent distortion upon being bent, i.e., a good shape memory, this material is disadvantageous from the standpoints of availability and cost, being about 15 times more expensive than stainless steel. Moreover, nickel-titanium is a difficult material to process, for example, in soldering or brazing other metal objects to it, such as protective coils. Further, when used in relatively long lengths, e.g., as the core portion of a guidewire, nickel-titanium is often considered too flexible, and when used in relatively short lengths, it is usually considered too stiff and likely to perforate the wall of a passageway.

In order to preserve the flexibility of the distal portion of a guidewire and yet protect it from physical damage, it is common, as indicated above, to surround the distal portion with an elongated (albeit tiny) metal coil which is anchored at one end to the core portion, and at the other end to the bulbous end of the wire's distal portion. The protective coil is commonly made from a monofilament of a relatively dense and, hence, radiopaque material, such as platinum, whereby the medical practitioner can easily follow the movement of the guidewire's distal end on a fluoroscope as he or she maneuvers the guidewire through an arterial passageway. While metal coils operate effectively in achieving their protective and flexibility-enhancing purposes, such coils are difficult to attach to the guidewire owing, in part, to their dissimilarity with the guidewire material. Further, prior art coils are disadvantageous from the standpoint of material cost.

SUMMARY OF THE INVENTION

In view of the foregoing discussion, one object of this invention is to provide an improved guidewire of the above type, one that is improved at least from the standpoints that it is torsionally stiffer and/or more fluoroscopically visible than conventional wires of the same diameter.

Another object of this invention is to provide an improved guidewire with increased tensile strength and flexibility.

A further object of this invention is to provide a catheter guidewire having better mechanical performance than the standard stainless steel monofilament and without the high cost of conventional NiTi alloy wire.

Still another object of this invention to provide a steerable, intravascular guidewire comprising a distal tapered tip having a less costly, yet equally radiopaque and flexible protective coil thereabout.

Briefly, in accordance with one aspect of this invention, a catheter guidewire comprises a plurality of equilength filaments which are intertwined about each other to form a "braid," much like a multifilament rope. Each filament of the braided guidewire has a transverse cross-section which compliments that of the other filament(s) of the braid so that the braided guide wire has a substantially circular transverse cross-section which is uniform over its entire length. Preferably, each of the filaments of the braided guidewire comprises a metal, and the metal material of each filament may be the same or different. According to a preferred embodiment, each of the filaments of a multifilament guidewire comprises stainless steel. Unexpectedly, such a guidewire was found to have a torsional stiffness significantly greater than that of a conventional stainless steel monofilament of the same material and diameter, and even higher than that of a monofilament of nickel-titanium of the same diameter. In accordance with another embodiment, at least one of the filaments of a multifilament guidewire comprises a material different from that of the others, e.g., one filament may comprise nickel-titanium and the others stainless steel, whereby one or more of the properties of the guidewire, e.g., torsional stiffness, fluoroscopic viewability, tensile strength, etc., may be tailored to satisfy of different applications. Preferably, small particles of a material of high density (e.g. gold or platinum dust) are applied to one or more filaments of the braid, or to the braid itself, whereby the radiopacity of the composite wire is further enhanced so that it can be more readily seen fluoroscopically. Alternatively, each filament of the braid, or the braid itself, is electroplated with a radiopaque metal to enhance its radiopacity. Preferably, the distal and core portions of the guidewire are integral (i.e., made from one piece), the distal portion being tapered in diameter, e.g., from a nominal diameter of between about 0.25 mm. to about 0.45 mm., down to about 0.05 mm.

In accordance with another aspect of the invention, the circular cross-section of the braided guidewire of the invention is achieved by repeatedly drawing a braid, composed of multiple filaments and having an irregularly shaped transverse cross-section, through a series of circular dies of progressively smaller diameter. In the resulting multifilament, "drawn round" wire, the filaments are bonded together by frictional and compressive forces. Preferably, a radiopaque material (e.g., gold or platinum dust) is applied to the wire filaments (e.g., by spraying or plating) prior to the drawing operation, whereby such material becomes entrapped in the intricacies (interior) of the braid and thereby enhances the radiopacity of the guidewire.

The multifilament catheter guidewire of the invention is advantageous in that (a) the core and distal portions can be integral, thereby eliminating the need and cost of designing and coupling discrete core and distal components, (b) with the addition of the radiopaque material to the braid, it can be made significantly more visible fluoroscopically than conventional monofilament guidewires of the same diameter and material, (c) it is structurally stronger and, hence, less apt to break or be damaged by normal use, (d) its steerability and other properties can be tailored for a particular application, and (e) it is torsionally stiffer than any conventional guidewire of the same diameter, whereby the steerability of the guidewire is exceptionally good.

According to another aspect of the invention, there is provided an improved catheter guidewire of the type comprising a coil which protects the distal end. According to a preferred embodiment, the coil is made of a multifilament, "drawn round" wire of the type from which the guidewire is made (but not necessarily comprising the same metal filaments).

The invention and its various aspects and advantages will be better understood and appreciated from the ensuing detailed description of preferred embodiments, reference being made to the accompanying drawings.

DETAILED DESCRIPTION OF PREFERRED EMBODIMENTS

Figure 1:
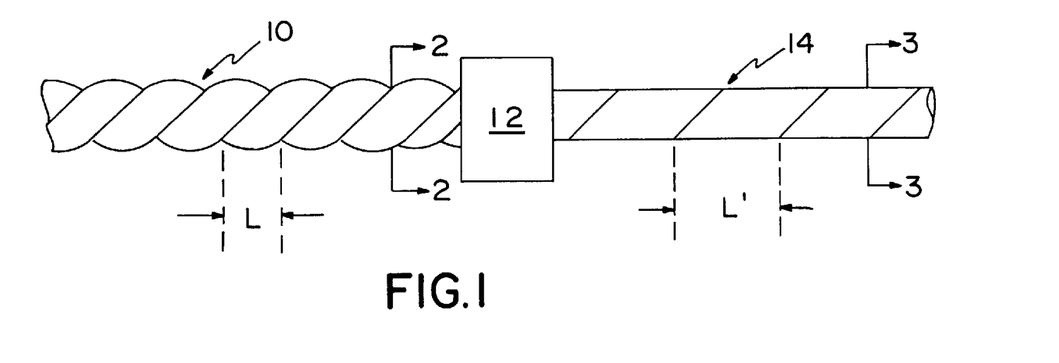
FIG. 1 illustrates a wire braid being drawn through a die to form a multifilament guidewire core structured in accordance with a preferred embodiment of the invention.

Referring now to the drawings, FIG. 1, schematically illustrates a multifilament wire "braid" 10 of irregular transverse cross-section (shown in FIG. 2) in the process of being pulled or drawn, in the direction of arrow A, through a conventional wire-drawing die 12 to produce a guidewire core 14 having a reduced cross-sectional area (compared to the cross-sectional area of the braid) which is substantially circular or "round" in shape. As used herein, "braid" is defined as a multifilament structure resulting from intertwining, preferably in an orderly fashion, two or more filaments about each other in the longitudinal direction.

Preferably, each of the individual filaments 15, 16 and 17 of braid 10 is of circular cross section, having a diameter of between about 0.10 and 0.50 mm., and most preferably about 0.25 mm. The "lay" length L of braid is 10 preferably between about 1.0 and 5.0 mm., and most preferably about 2.0 mm. After passing through the die, the overall diameter of the resulting "multifilament drawn-round" (MFTR) guidewire is preferably between about 0.25 and 0.45 mm., and most preferably about 0.35 mm., and the lay length L' is increased by more than 50%, depending on braid's cross-sectional size reduction, as effected by the drawing operation. By varying the initial lay length L, it is possible to vary the flexibility of the MFDR guidewire of the invention. As indicated above, the wire-drawing die 12 is of conventional design, such as those commercially available from Woodburn Diamond Die, Inc., Woodburn, Ind., and wire-drawing machines that utilize such dies are well known. While die 12 is illustrated as converting a braid having the irregular transverse cross-section shown in FIG. 2 to the circular cross-section of FIG. 3 in a single pass, the conversion to a circular cross-section usually requires repeated drawing, e.g., 3 to 4 times, through progressively smaller die apertures, depending on the softness of the metal filaments. In this embodiment the guidewire core 14 is drawn round, but other cross sectional shapes (e.g., elliptical, triangular, rectangular, hexagonal, etc.) may be achieved by using a die with the appropriately shaped output aperture.

Thus, the multifilament guidewire of the invention is formed by twisting a plurality of wire filaments together to form the wire braid 10, and subsequently drawing the braid through the die 12. During the drawing operation, tension is maintained on the braid to prevent the filaments from "bunching-up" at the die entrance. After the wires are drawn, the resulting MFDR guidewire 14 is cut and straightened, and later ground, assuming a tapered distal end is desired. Taper or other reductions in cross sectional area can be also achieved through chemical milling. Once grinding or milling is complete, the multifilament guidewire is annealed to relieve stress in the wire. Stresses are reduced by exposing the guidewire to a temperature ranging from 650 to 950 degrees F. over a period of time ranging from six to twenty-four hours, depending on the filament materials. The time required to reduce stresses can be shortened by increasing the temperature.

Figure 3:
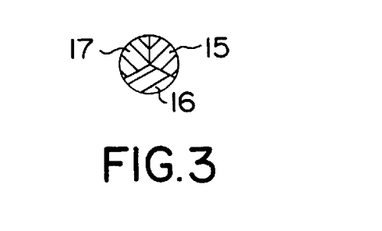

In FIGS. 1 and 3, braid 10 and the MFDR guidewire 14 resulting from the drawing operation are illustrated as comprising, and preferably do comprise, a total of three individual filaments 15, 16 and 17; it will be appreciated, however, that the number of filaments may comprise as few as two filaments, and up to as many filaments as desired. As shown in FIG. 3, each of the substantially cylindrically-shaped filaments of the wire braid 10 is crushed by the dye so as to have cross-sectional shape, shown illustratively as a sector of a circle, which compliments the respective cross-sectional shapes of the other filaments of the multifilament guidewire, whereby the preferred circular transverse cross-section of the guidewire is achieved. As a result of the compressive forces exerted on the braid during the drawing operation, the metal filaments of the multifilament guidewire adhere to each other by frictional and other physical forces.

According to a first preferred embodiment of the invention, all of the filaments of the multifilament guidewire comprise the same metal material, preferably either 304V, MP35N, L-605, or Elgiloy stainless steels, or a nickel-titanium alloy. Very surprisingly, it has been found that multifilament guidewires of the type described herein exhibit certain characteristics which differ markedly from their monofilament counterparts, i.e., single strand wires of the exact same material and diameter. For example, the torsional stiffness of a multifilament guidewire of 304V stainless steel having a diameter of 0.3 mm. (as produced by the drawing process described above) has been measured to be several times greater than that of a monofilament of the same material and diameter. Thus, when each of these guidewires is torqued at a location spaced about 1 meter from a free end, the multifilament guidewire of the invention will transmit about the same torque angle to its free end, whereas the monofilament wire will transmit only a small fraction of the torque angle to its free end. Moreover, the multifilament guidewire will transmit the same torque angle when rotated in either direction, clockwise or counter-clockwise; this is not necessarily expected since the filaments of the MFDR guidewire are wound in one direction, either clockwise or counter-clockwise. Further, the flexibility of the multifilament stainless wire has been found to be about 50% greater than the monofilament, as measured by the axial force (applied to a wire's free end) required to cause the wire to prolapse. Thus, while having lower pushability or stiffness compared to a stainless steel monofilament, the multifilament stainless guidewire of the invention has sufficient stiffness to traverse most lesions, and sufficient flexibility to follow arterial passageways without traumatizing the walls thereof As noted above, the flexibility of the MFDR guidewire can be adjusted to some extent by varying the lay length of the braid 10.

In addition to the advantages noted above, the multifilament guidewire of the invention affords certain other unanticipated advantages. For example, the aforementioned stainless steel multifilament guidewire has been found to exhibit an exceptionally high number of "turns to failure," a physical test required by the Federal Drug Administration in approving guidewires for human applications. According to this test, one end of the wire is held stationary (clamped) in a test fixture while a continuous torque is applied to the wire at a location about 75 cm. from the clamped end. While a monofilament of 304V stainless steel typically fails (breaks) after about 5 turns, the multifilament guidewire of the invention, made of the same material and having the same diameter, was observed to fail after about 47 turns. Moreover, while a monofilament wire, when ground to a diameter less than 50% of its initial diameter (e.g., for use as the distal portion of the guidewire), tends to "pigtail" after the grinding process and requires heating (annealing) at high temperatures (e.g., 800 degrees F.) for 2–3 hours to relieve stress so that the wire straightens, the multifilament guidewire of the invention exhibits no such "pig-tailing" and, hence, requires no stress-relieving process. This is a major advantage from a manufacturing cost standpoint.

According to a second preferred embodiment of the invention, at least one of the metal filaments of the multifilament guidewire 14 comprises a material which differs from the material of the other filaments, whereby the properties of the "composite" wire can be adjusted, to some extent, to achieve a desired performance characteristic. Such properties can be density, tensile strength, hardness, flexibility, torsional rigidity, etc. For example, multifilament guidewires of nickel-titanium and 304V stainless steel have been produced which exhibit characteristics unlike those of any monofilament wires or, for that matter, any multifilament wires in which the filaments comprise the same material. Such a "hybrid" guidewire was made by intertwining one filament of nickel-titanium with two filaments of 304V stainless steel, all having a diameter of about 0.25 mm., and drawing the resulting braid through a series of circular dies to produce an MFDR guidewire of substantially circular cross-section having a diameter of 0.325 mm. The resulting guidewire was stress relieved (annealed) at a temperature of between 1100 and 1300 degrees F. Surprisingly, the wire exhibited excellent shape memory, a characteristic of nickel-titanium. Note, it was expected that the composite wire would loose its shape memory as a result of heating it to the temperature required for annealing stainless steel, which is more than 100 degrees higher than the normal annealing temperature for nickel-titanium. But, because the filaments were "cold-worked," the annealing temperature of nickel-titanium was increased without degrading the alloy's desirable superelastic properties. Nitinol (Nickel 50%/Titanium 50%) exhibits superelastic properties which makes it highly flexible. It fully recovers large strains (5 to 10%). This recovery is principally due to a stress-induced phase transformation from austenitic to martensitic. The stress-induced phase transformation reverses upon release of stress. Thus, by combining a filament of nickel-titanium with two filaments of MP35-N stainless steel, the composite has enhanced strength and a considerable amount of recovery (shape memory) when deformed, thereby providing a guidewire with relatively high resistance to kinking.

As suggested above, a particular advantage afforded by the multifilament structure of the guidewire shown in FIGS. 1 and 3 is that the "composite" wire (collectively defined by the properties by the individual filaments 15–17) can be made to have properties unlike those of any individual material. As an example of the utility of this concept, suppose a user is required to cross a lesion or pass an occlusion in feeding the guidewire along a desired passageway. In this case, the guidewire needs to be able to sustain substantially more axial and rotational forces without permanent deformation. Often, the distal portion of the tip will buckle or kink. Therefore, the only way to proceed with the procedure is by exchanging the guidewire being used with a stiffer and larger diameter wire which allows the user to push harder. In contrast, by providing multifilament wires of different materials, the user can choose from various guidewires with similar diameter but with higher or lower stiffnesses, thus reducing the probability of causing injury to an artery. The wire drawing operation produces a metal composite of reduced cross-sectional area with different mechanical characteristics based on the composition of each of the wires that make the composite. An important and highly desirable attribute of MFDR guidewires comprising different alloys as filaments is that the composite wire will have mechanical properties, such as tensile strength, modulus of elasticity, shear strength, and hardness, that differ from those properties of any of the constituent filaments. MFDR guidewires have been made from different types of stainless steel, for example, one filament of L-605 stainless and two filaments of MP35-N stainless.

Figure 2:
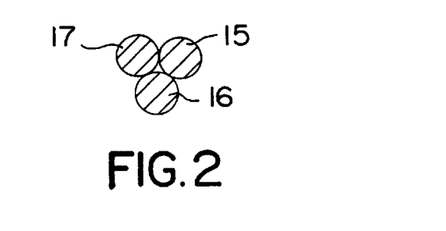
FIGS. 2 and 3 are cross-sectional views of the wire braid and guidewire shown in FIG. 1, taken along the section lines 2—2 and 3—3, respectively.
Figure 4:
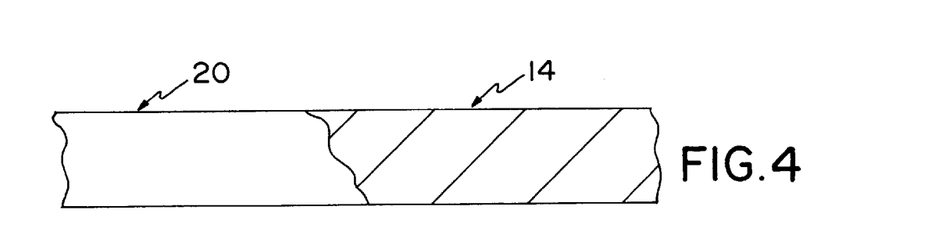
FIG. 4 illustrates the guidewire core of FIGS. 1 and 3 with a lubricious jacket or coating.
Figure 5:
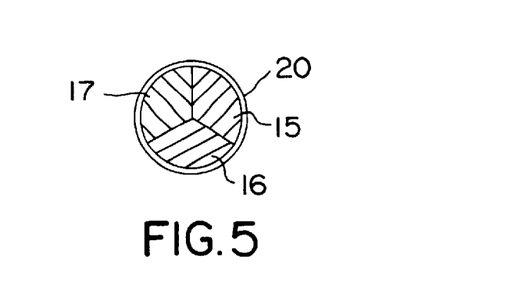
FIG. 5 is a cross-sectional illustration of the guidewire shown in FIG. 4 taken along the section line 5—5.

Referring now to FIGS. 4 and 5, the guidewire 14 shown in FIGS. 1–3 is shown as further comprising a compliant jacket or coating 21 which enhances the column strength of the wire. Preferably, such jacket or coating comprises a hydrophilic material, preferably a thermoplastic material, such as polyurethane, as disclosed in the commonly assigned U.S. application Ser. No. 08/766,976, filed on Dec. 16, 1996 in the name of F. J. Avellenet. The compliant jacket or coating is fitted tightly over the guidewire 14 by various techniques, such as by co-extrusion, casting, insert molding, spraying, or dipping. FIG. 5 illustrates the transverse cross-section of the wire shown in FIG. 4.

Figure 6:
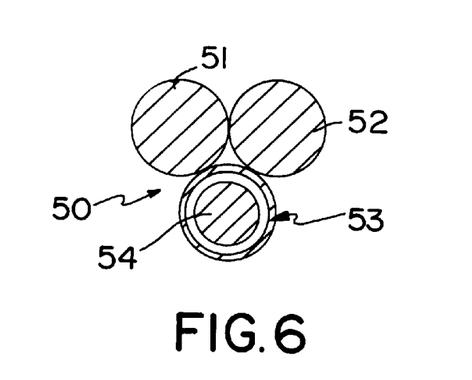
FIGS. 6 and 7 schematically illustrate cross-sections of an alternative braid before and after being drawn through a die, respectively.
Figure 7:
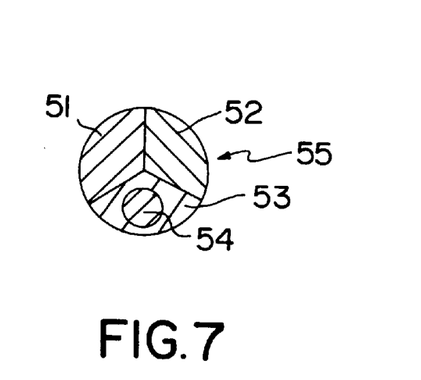

Referring now to FIGS. 6 and 7, there is shown a cross section of a braid 50 comprising three filaments 51–53. Two filaments (e.g., 51 and 52) are made of the same metal alloy, preferably MP35-N stainless steel, and a third filament 53 comprises a hollow metal tube 53A, preferably of the same stainless steel material, which contains a wire 54 of denser metal, preferably tantalum, platinum or gold. The three filaments of the braid are drawn through a die 10 to produce the MFDR guidewire of the invention. A transverse cross-section of the resulting MFDR guidewire is shown in FIG. 7. As shown in FIG. 7, tube 53A collapses around the internal dense wire 54 as a result of the drawing operation. The resulting MFDR guidewire is, as a result of the dense wire 54, considerably more radiopaque than an MFDR wire comprising three filaments of the stainless steel or NiTi alloy. Tantalum wire-filled tubes 54 can be obtained from such vendors as Fort Wayne Metals of Fort Wayne, Ind. As an alternative to filling tube 53A with a dense material which remains inside the tube after the drawing process to enhance the radiopacity of the MFDR wire, tube 53A can be initially filled with an aluminum wire which, after drawing, can be removed, e.g., by a conventional etching process. Thus, after removal of the aluminum wire, tube 53A can be used, e.g., to infuse dilating drugs or a contrast medium to a desired location in the arterial passageway.

Figure 8:
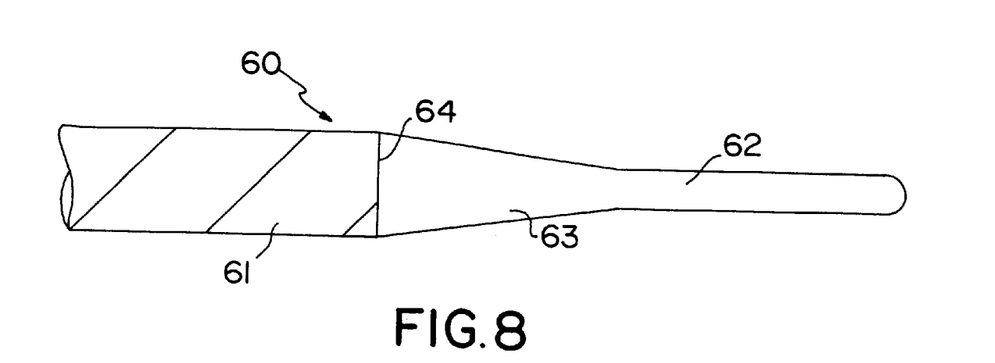
FIG. 8 is a side view of a guidewire having a multifilament, drawn round core and a metal monofilament tip at its distal end.

Referring to FIG. 8, there is shown a side view of a guidewire 60 having a MFDR core 61 and a metal monofilament tip 62 at its distal end. The core 61, which may comprise a combination of any of the metal filaments discussed above, is connected to the tip 62 by a tapered portion 63 which is butt coupled to the core by a suitable joint 64. The taper 63 and the tip 62 are both be made from a suitably ground monofilament of stainless steel or NiTi alloy.

Figure 9:
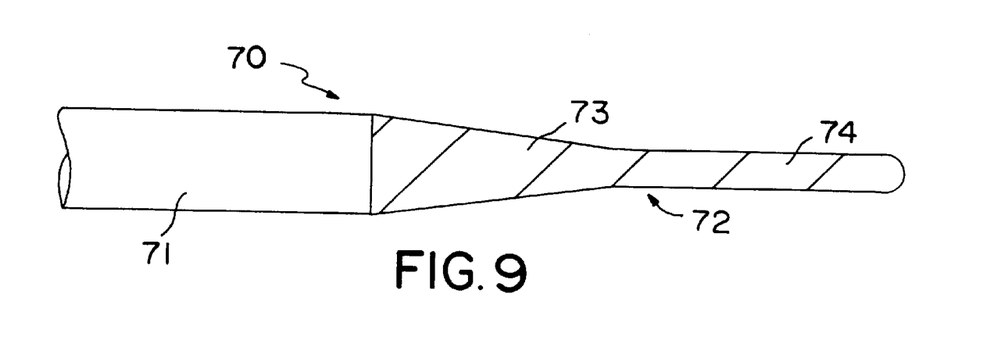
FIG. 9 is a side view of a guidewire having a metal monofilament core and multifilament, drawn round tip at its distal end.

In FIG. 9, there is shown a side view of a guidewire 70 having a metal monofilament core 71, preferably of stainless steel or NiTi alloy, and a MFDR distal end 72 comprising a suitably ground tapered portion 73 and a tip 74.

Figure 10:
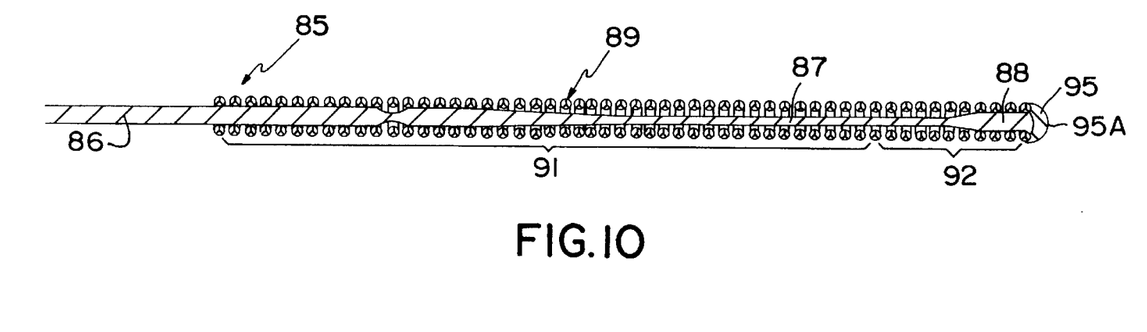
FIG. 10 is a side view of a unitary multifilament, drawn round guidewire.

In FIG. 10, a guidewire 85 embodying the invention is shown as comprising a unitary (one-piece) MFDR wire comprising a core portion 86 having a diameter of about 0.33 mm. that has been suitably ground or milled at one end by conventional techniques to define a distal portion 87 which tapers down to about 0.075 mm. at its smallest diameter. The distal portion is expanded at the very tip 88 to a diameter of about 0.25 mm. Owing to the flexibility of the MFDR wire, the guidewire may be used without a protective coil. However, if a coil 89 is desired, it may be made from a suitably coiled MFDR wire of any of the metal filaments described above, including ones which includes a wire-filled tube. Alternatively, the coil may be wound from a monofilament of platinum/iridium, tantalum or stainless steel. As another alternative, the coil 89 may comprise two discrete sections, as shown, a relatively long section 91, about 25 cm. in length, made of stainless steel, and a much shorter section 92, about 2.5 cm. in length, made of a more flexible material such as platinum-iridium. To provide a soft tip, coil section 92 preferably extends a short distance beyond the very end of the distal portion 87, e.g., by a few millimeters, to define a cavity which can be filled with a soft elastomeric material 95 which is molded so as to terminate in a rounded end 95A.

Figure 11:
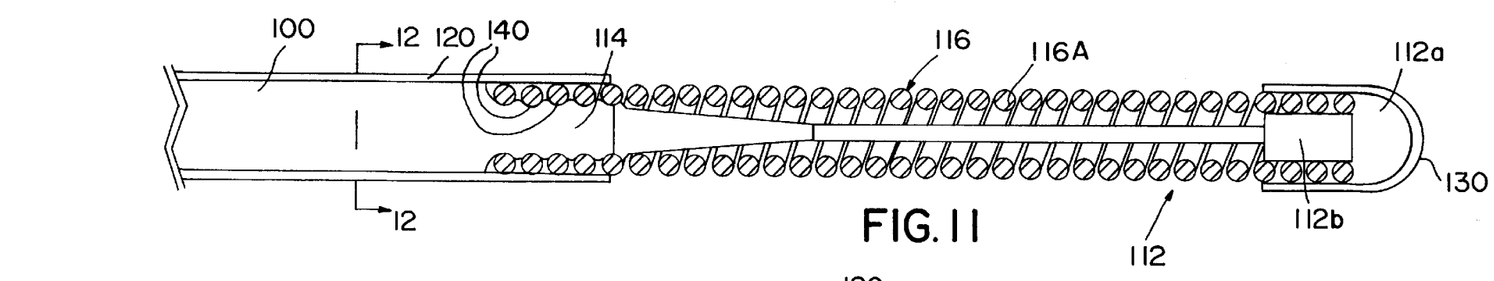
FIG. 11 is a side view of a guidewire having multifilament, drawn round core and distal portions, and a plastic-coated metal coil, shown in cross-section.
Figure 12:
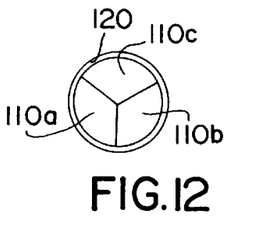
FIG. 12 is a cross-sectional view of the core portion of the FIG. 11 guidewire.

FIG. 11 illustrates an embodiment of a MFDR guidewire that includes a coil 116 composed of a helically wound strand 116a of an appropriate metal, or metal alloy, or an appropriate organic polymeric material, such as polyurethane, which may be coated with a layer of a hydrophilic lubricious material such as polyvinylpyrolidone, polyethyleneoxide and/or poly(2-HEMA). The core wire 100 of this embodiment is formed by a drawn round wire including three strands 110*a*, 110*b* and 110*c* as shown in FIG. 12. The core wire is preferably encased within a compliant jacket 120 comprising a hydrophilic lubricious material. By constructing the core wire 100 from two or, preferably, three filaments or strands, a drawn round wire having greater tensile strength but more flexibility and lower cost than a superelastic metallic member having a solid cross-section in a monofilament form as previously used is provided. The use of a bifilament or trifilament core wire rather than a monofilament core wire, therefore, is preferred.

The distal tip 112 shown in FIG. 11 includes a substantially hemispherical portion 112*a* and a substantially cylindrical portion 112*b* extending away from the hemispherical portion 112*a* towards the proximal end of the guidewire. As FIG. 11 shows, the outer surface of the cylindrical portion 112*b* and the step lace defining a transition section between the portions 112*a* and 112*b* of the distal tip 112, form a seat for an end of the coil 116. The distal tip 112 is also encased within a compliant jacket 130 including the hydrophilic lubricious material mentioned above. The jacket or sheath 120 and the jacket or sheath 130 do not extend over the coil 116 beyond the anchored (non-flexing) ends of the coil. Thus, the entire guidewire, excluding the operative, i.e., flexing, section of the coil 116, is encased within a compliant jacket of or including the lubricious coating. The transition segment 114 of the embodiment shown in FIGS. 11 and 12 may include spiral grooves 140 defined therein. The coil 116, therefore, may be threaded onto the core wire with the spiral grooves 140 facilitating retention of the end of the coil. The cylindrical portion 112*b* of the tip 112 may include similar spiral grooves, if desired.

While the invention has been described with reference to particularly preferred embodiments, it will be appreciated that modifications can be made without departing from the spirit of the invention, and such variations are intended to fall within the scope of the appended claims.

What is claimed is:

1. A catheter guidewire comprising:
   a plurality of metal filaments which have been twisted about each other to form a multifilament wire, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire; and
   a hydrophilic low friction material over the length of the wire.

2. The catheter guidewire as defined by claim 1 wherein all of said filaments comprise the same metal material.

3. The catheter guidewire as defined by claim 1 wherein said material is selected from the group consisting of stainless steel and nickel-titanium.

4. A catheter guidewire comprising:
   a plurality of metal filaments which have been twisted about each other to form a multifilament wire, at least one metal filament comprising a material different from that of the other metal filaments, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire.

5. A catheter guidewire comprising:
   a plurality of metal filaments which have been twisted about each other to form a multifilament wire, one of said filaments comprising a metal tube filled with a radiopaque material, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire.

6. A catheter guidewire comprising:
   a plurality of metal filaments which have been twisted about each other to form a multifilament wire which entraps particles of a radiopaque material, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire.

7. The catheter guidewire as defined by claim 6 wherein said particles are selected from the group consisting of gold, platinum and barium sulfate.

8. A guidewire comprising:
   a plurality of metal filaments which have been twisted about each other to form a multifilament wire, at least one metal filament comprising a material different from that of the other metal filaments, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire.

9. The guidewire as set forth in claim 1 wherein the plurality of filaments are together drawn through a die to produce a guidewire core having a reduced diameter.

10. A guidewire comprising:
    a plurality of metal filaments which have been twisted about each other to form a multifilament wire having a proximal end and a distal end that is smaller in diameter than said proximal end, each filament of said multifilament wire having a transverse cross-section which complements that of the other filament(s) so that said multifilament wire has a substantially circular transverse cross-section which is substantially uniform over a length of the multifilament wire, said circular transverse cross-section, and which defines a diameter which is appropriate for a guidewire.

11. A method for making a catheter guidewire having a proximal end and a distal end, the method comprising the steps of:
    twisting a plurality of metal filaments together;
    drawing the twisted metal filaments through a die to produce a guidewire core having a reduced diameter; and
    using the guidewire core in forming a guidewire.

12. The method of claim 11, further comprising the step of either (i) applying radiopaque particles to said filaments prior to drawing through said die, whereby said particles become entrapped within said mulifilament guidewire and enhance the radiopacity thereof, or (ii) plating said guidewire core with radiopaque particles.

13. The method of claim 11, further comprising the step of grinding the guidewire core to reduce at least a portion of the diameter of the guidewire core.

14. The method of claim 13, further comprising the step of grinding the distal end of the guidewire core to produce a tapered tip for the guidewire.

15. The method of claim 13, wherein the step of grinding the distal end is done by electrochemical machining of the distal end.

16. The method of claim 14, further comprising the step of plating the distal end with a radiopaque material.

17. An intravascular guidewire for guiding medical devices through arterial passageways, said guidewire comprising a multifilament, drawn round core portion terminating in a flexible distal end of reduced diameter.

18. The guidewire as defined by claim 17, further comprising a protective coil made from a helically wound multifilament wire.

19. The guidewire as defined by claim 17, further comprising a protective coil comprising two monofilaments of dissimilar materials which are butt coupled together and helically wound to form an integral coil.

20. A catheter guidewire according to claim 1, wherein:
none of said plurality of metal filaments forms a central core filament of said multifilament wire.

21. A catheter guidewire, comprising:
a plurality of metal filaments which have been twisted about each other to form a multifilament wire, said filaments each provided with a non-circular transverse cross-section such that each said filament complements that of the other filament(s) so that said multifilament wire has a substantially circular transverse cross-section which is substantially uniform over a length of the multifilament wire, said circular transverse cross-section defining a diameter which is appropriate for a guidewire; and
a low friction material over the length of the wire.

22. A catheter guidewire, comprising:
a plurality of metal filaments which have been twisted about each other to form a multifilament wire, none of said plurality of metal filaments forming a central core filament of said wire, and each filament of said multifilament wire having a transverse cross-section which complements that of the other filaments so that said wire has a substantially circular transverse cross-section which is uniform over a length of the wire, said circular transverse cross-section defining a diameter which is appropriate for a guidewire; and
a low friction hydrophilic material over the length of the wire.

23. A catheter guidewire according to claim 22, wherein:
said low friction material forms a sheath extending over the length of the wire.

24. A catheter guidewire, comprising:
a plurality of metal filaments which have been twisted about each other to form a multifilament wire having a first diameter over a length of the wire, and then drawn through at least one die to form a cable provided with a second diameter smaller than said first diameter over a length of the cable, said second diameter being appropriate for a guidewire.

25. A catheter guidewire according to claim 24, further comprising:
a low friction sheath extending over the length of the cable.

26. A catheter guidewire according to claim 25, wherein:
said sheath is hydrophilic.

27. A catheter guidewire comprising:
a plurality of metal filaments which have been twisted about each other to form a multifilament wire, each filament of said multifilament wire having a transverse cross-section which complements and is substantially the same as that of the other filament(s) so that said multifilament wire has a substantially circular transverse cross-section which is substantially uniform over a length of the multifilament wire, which is solid at a center of said circular transverse cross-section, and which defines a diameter which is appropriate for a guidewire.

28. A catheter guidewire according to claim 21, wherein:
none of said plurality of metal filaments forms a central core filament of said multifilament wire.

* * * * *